(12) United States Patent
Tsujii

(10) Patent No.: US 6,507,038 B2
(45) Date of Patent: Jan. 14, 2003

(54) IMAGE SENSING APPARATUS

(75) Inventor: Osamu Tsujii, Utsunomiya (JP)

(73) Assignee: Canon Kabushiki Kaisha, Tokyo (JP)

Subject to any disclaimer, the term of this patent is extended or adjusted under 35 U.S.C. 154(b) by 0 days.

(21) Appl. No.: 10/000,402

(22) Filed: Dec. 4, 2001

(65) Prior Publication Data

US 2002/0096652 A1 Jul. 25, 2002

Related U.S. Application Data

(62) Division of application No. 09/491,962, filed on Jan. 27, 2000, now Pat. No. 6,396,074.

(30) Foreign Application Priority Data

Jan. 26, 1999 (JP) ............................................. 11-017462

(51) Int. Cl.⁷ ................................................. A61B 6/00
(52) U.S. Cl. ......................... 250/582; 250/580; 250/584
(58) Field of Search .............................. 250/582, 580, 250/584, 583, 581, 585, 586, 591

(56) References Cited

U.S. PATENT DOCUMENTS 5,289,012 A * 2/1994 Alvarez ....................... 250/582
6,396,074 B1 * 5/2002 Tsujii ........................... 250/582

FOREIGN PATENT DOCUMENTS

| JP | 55-012429 | 1/1980 |
| JP | 56-011395 | 2/1981 |

* cited by examiner

Primary Examiner—Hung Xuan Dang
(74) Attorney, Agent, or Firm—Fitzpatrick, Cella, Harper & Scinto

(57) ABSTRACT

The gain correction image is composed of a grid-free image regardless of the presence or absence of the grid or the kind thereof. The gain correction images are stored in the image memory unit, and, under the control of the pre-process unit and according to the result of the grid detection means, reference is made to the image process parameter table stored in the image process parameter memory unit and the matching gain correction image is downloaded from the image memory unit.

24 Claims, 4 Drawing Sheets

IMAGE SENSING APPARATUS

This application is a division of application Ser. No. 09/491,962, filed Jan. 27, 2000, now U.S Pat. No. 6,396,074.

BACKGROUND OF THE INVENTION

1. Field of the Invention

The present invention relates to an image sensing apparatus capable of sensing an image with a grid.

2. Related Background Art

When a certain fluorescent material is irradiated with radiation such as X-ray, $\alpha$-ray, $\beta$-ray, $\gamma$-ray, electron beam or ultraviolet light, a part of the radiation energy is accumulated in the fluorescent material. It is already known that, by irradiating the fluorescent material with exciting light such as visible light, the fluorescent material shows exhaustive light emission according to the accumulated energy, and the fluorescent material showing such property is called accumulating or exhaustive fluorescent material.

Conventionally there is already known a system of utilizing such accumulating fluorescent material, recording the radiation image information of an object such as human body on a sheet of the accumulating fluorescent material, then scanning the accumulating fluorescent sheet with exciting light such as laser beam to induce emission of the exhaustive florescent light and photoelectrically reading such light emission to obtain image signal. A radiation image information recording/reproducing system, for outputting the radiation image of the object on a recording material such as a photographic sensitive material and a display apparatus such as a cathode ray tube based on such image signal is disclosed for example in the Japanese Patent Application Laid-open No. 55-12429 and 56-11395, for example.

Also in recent years, there is being developed an apparatus for sensing the X-ray image utilizing a semiconductor sensor. In comparison with the radiographic system utilizing the conventional silver halide-based photography, such system has a practical advantage of recording the image over an extremely wide exposure range. Such system reads the X-ray of an extremely wide range with photoelectric conversion means and converts it into the electrical signal. It is thus rendered possible to obtain a visible radiation image not affected by change in the radiation dose, by outputting such electrical signal to a recording material such as a photographic recording material or a display apparatus such as a cathode ray tube.

In the analog image sensing with the above-described conventional accumulating fluorescent material, there are employed various grids for reducing the scattered ray at the image sensing, but, in the digital image data utilizing semiconductor sensor, there are generated Moire fringes and shading phenomenon because of the relationship between the sampling pitch and the grid frequency. One of the reasons causing such shading, in case of a moving grid, is the difference in the image collecting time at the gain image sensing and the object sensing, whereby the mode of grid movement is different to generate a special pattern.

SUMMARY OF THE INVENTION

The object of the present invention is to provide an image sensing apparatus capable of providing an image without shading in case of image sensing with a grid.

The above-mentioned object can be attained, according to aspect of the present invention, by an image sensing apparatus comprising sensor means for detecting the distribution of radiation transmitted by an object; grid attaching/detaching means for attaching and detaching a grid for reducing the scattered ray of the radiation; and image process means for effecting an image process on image data collected by the sensor means and outputting the processed image data; wherein, in executing gain correction in the image process means, an image without using a grid is used for gain correction regardless whether the grid is used or not.

According to another aspect of the present invention, there is also provided an image sensing apparatus comprising sensor means for detecting the distribution of radiation transmitted by an object; grid detection means for detecting the kind and presence/absence of a grid for reducing scattered ray of the radiation; and image process means for effecting an image process on image data collected by the sensor means and outputting the processed image data; wherein, in executing gain correction in the image process means, an image without using grid is used for gain correction regardless of the kind of the grid.

According to still another aspect of the present invention, there is also provided an image sensing apparatus comprising sensor means for detecting the distribution of radiation transmitted by an object; and image process means for effecting an image process on image data collected by the sensor means through a grid for reducing the scattered ray of the radiation and outputting the processed image data; wherein, in executing gain correction in the image process means, an image without using grid is used for gain correction.

Still other objects of the present invention, and the features thereof, will become fully apparent from the following description, which is to be taken in conjunction with the attached drawings.

DESCRIPTION OF THE PREFERRED EMBODIMENTS

Figure 1:
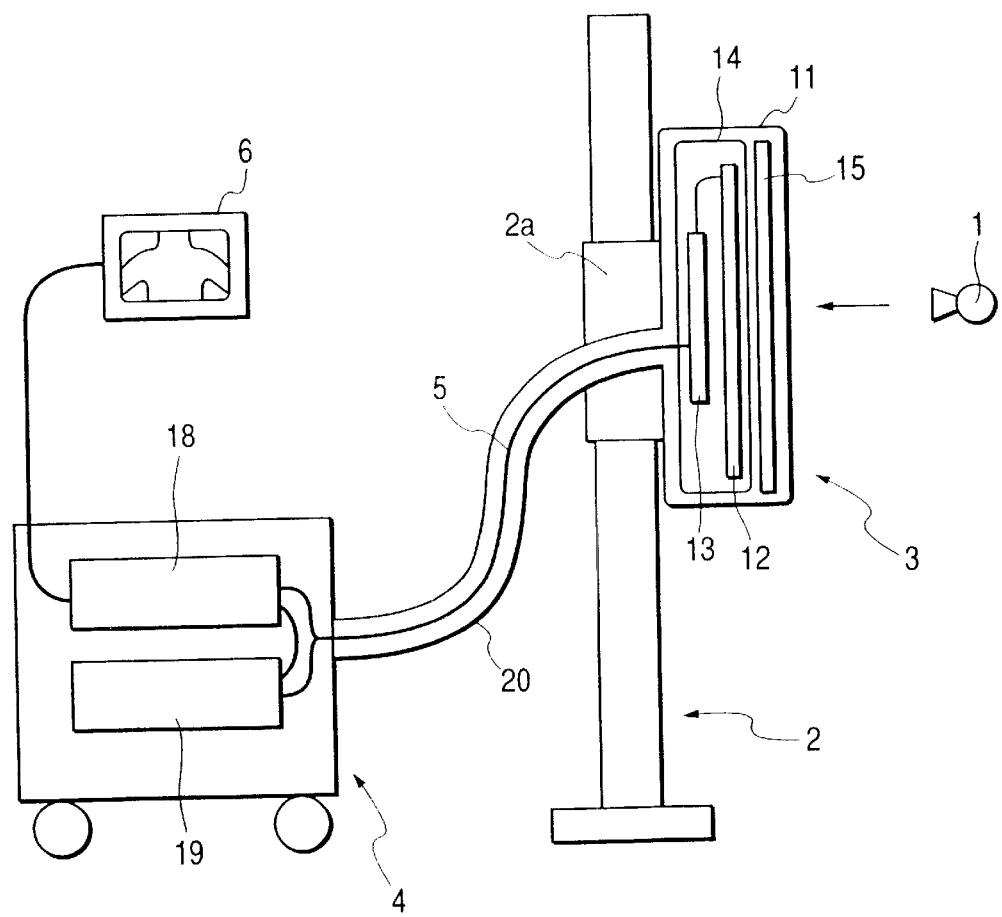
FIG. 1 is a schematic view of an embodiment of the present invention.
Figure 2:
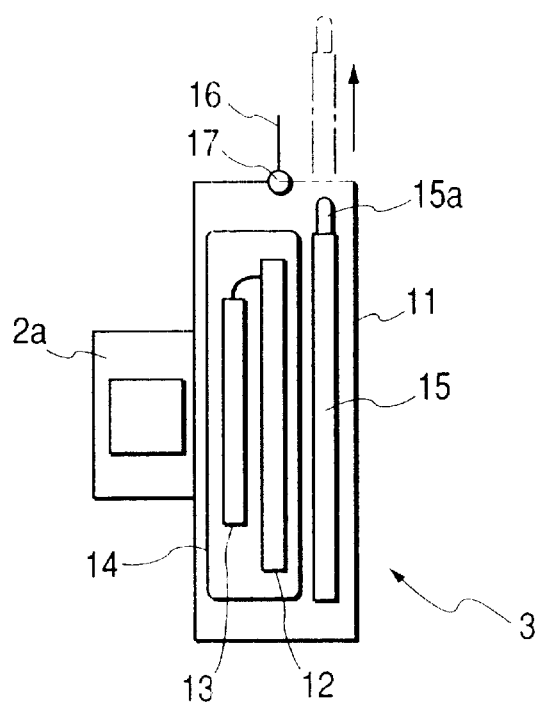
FIG. 2 is a plan view of an x-ray image taking unit.

FIG. 1 is a schematic view of a digital X-ray image sensing apparatus while FIG. 2 is a plan view of the X-ray image sensing apparatus, wherein the apparatus is composed of an X-ray generation unit 1, a support 2, an X-ray image sensing unit 3, a control unit 4 therefor, a cable 5 connecting the X-ray image sensing 3 and the control unit 4, and a monitor 6 for displaying the signal processed in the control unit 4.

The X-ray image taking unit 3 is vertically movable through a movable unit 2a of the support 2, and can thus be arbitrarily adjusted in height according to the position of the object, whereby there can be sensed the image of a predetermined position of the object positioned between the X-ray image sensing unit 3 and the X-ray generation unit 1.

A casing 11 of the X-ray image sensing unit 3 contains an X-ray image receiving unit 14 consisting of a radiation image detector 12 and a reading circuit 13 for reading signals from the radiation detector 12, and a grid unit 15 including a grid for eliminating the scattered light from the object. On a side of the grid unit 15 there is mounted a handle 15a, and, on a lateral face of the X-ray image sensing unit 3, an openable cover 16 is mounted through a hinge 17.

The grid unit 15 and the X-ray image receiving unit 14 are positioned in parallel inside the casing 11 of the X-ray image sensing unit 3, and the grid unit can be taken out from the X-ray image sensing unit 3 by opening the cover 16 and pulling the handle 15a.

The control unit 4 is composed of an image process unit 18 for effecting filter processes for noise reduction, edge enhancement etc. on the digital image signal supplied from a memory circuit 12, and a power source unit 19 for supplying electric power to the X-ray image receiving unit 14 and the image process unit 18. The X-ray image taking unit 3 and the control unit 4 are connected through the cable 5 consisting of a signal line and a power supply line, and covered and protected by a flexible tube 20. As the flexible tube 20 is composed of a flexible material, it can following the vertical movement of the X-ray image sensing unit 3.

In the X-ray image sensing system of the above-described configuration, the X-ray image sensing unit 3 is moved to a position to be sensed of the patient, and the image is sensed by emitting X-ray from the X-ray generation unit 1. The image information of the object, sensed in the X-ray image sensing unit 3, is transferred as a digital signal through the cable 5 to the image process unit 18, and is subjected therein to various image processings according to the presence/absence of use of the grid and the kind thereof.

Figure 3:
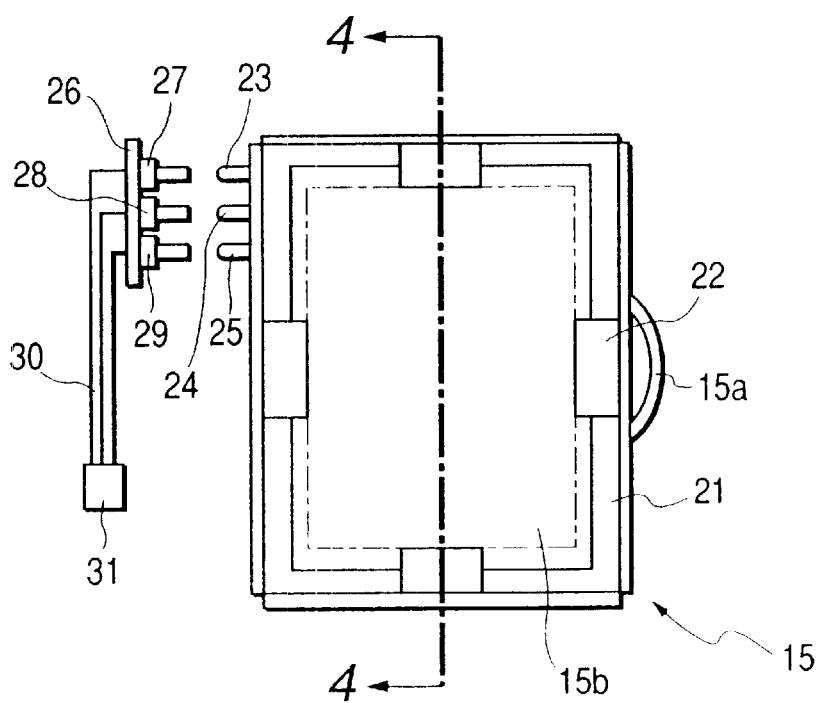
FIG. 3 is an elevation view of a grid.
Figure 4:
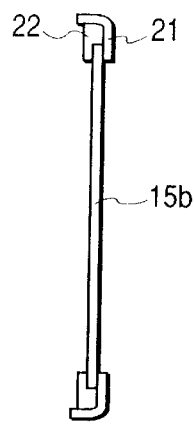
FIG. 4 is a cross-sectional view along a line 4—4 in FIG. 3.

FIG. 3 is an elevation view of the grid unit 15, while FIG. 4 is a cross-sectional view along a line 4—4 in FIG. 3. The grid unit 15 is composed of a handle 15a, a grid body 15b and a grid holder 21. The grid body 15b is fixed, by means of fixing members 22, to the frame-shaped grid holder 21, of which four sides are formed by rectangular bending in order to increase the strength. Among such sides formed by bending, a side opposed to the handle 15a is provided, at an end of the lateral face thereof, with projections 23, 24, 25 with equal gaps therebetween. Inside the X-ray image sensing unit 3 there is provided a switch mounting plate 26, on which provided are microswitches 27, 28, 29 so as to be opposed to the projections 23, 24, 25, and the microswitches 27, 28, 29 are connected to a grid discrimination circuit 31 through lead wires 30.

When the grid unit 15 is mounted in the X-ray image sensing unit 3, the microswitch 27 is shifted from off state to on state by the projection 23 on the grid holder 21. Similarly, the microswitches 28, 29 are respectively turned on respectively by the projections 24, 25. The on/off states of the microswitches 27, 28, 29 are transmitted through the lead wires 30 to the grid discrimination circuit 31 for discriminating the presence or absence of the grid body 15b and the kind thereof.

For example, the mounting of the grid body 15b of a 1st property A is identified if all the microswitches 27, 28, 29 are on, while the mounting of the grid body 15b of a 2nd property B is identified if the microswitch 27 alone is on, and the absence of the grid body 15b is identified if all the microswitches 27, 28, 29 are turned off.

Such setting is not limited to the above-described example but may be modified in various manners by the combinations of on/off states of the microswitches 27, 28, 29. Also the detection means is not limited to the microswitch but may also be composed of a lead switch utilizing magnetic force or a photoswitch utilizing light, and the number of the detection means may be suitably selected according to the necessity.

In the foregoing there has been explained the case of using a still grid body 15b, but such detection method may also be applied to an image sensing unit in which the grid body 15b is moved relative to the X-ray image receiving unit 14 at the image sensing operation. For example, by providing drive means such as a motor for moving the grid body 15b in the X-ray image sensing unit 3 and forming the grid body 15b so as to be movable relative to the grid holder 21, the grid body 15b alone can be moved at a predetermined speed by the drive means at the image sensing operation.

In such configuration, the detection means provided in the grid holder 21 may be utilized without change in the same manner as in the foregoing embodiment, in order to identify the presence/absence of the grid and the property of the grid body 15b, independently from the movement thereof.

Such detection means, provided not directly on the grid body 15b but on the common grid holder 21, can provide the following advantages. Regardless of the grid thickness which is dependent on the grid ratio, the grid inserting unit in the image sensing unit can be simplified to a same shape. Also in case of image sensing with moving of a grid, the durability is improved because the microswitches are not repeatedly turned on and off at each grid movement. Also the grid can be protected in attaching or detaching the grid to or from the image taking unit. Furthermore, by detecting the presence of the grid body 15b in the X-ray image sensing unit 3 and activating the grid drive means only in case of image sensing with moving of the grid, it is made possible to prevent erroneous activation of the grid drive means in a state where the grid body 15b is absent in the X-ray image sensing unit 3 or in case of image sensing with fixed grid.

Also the above-described grid detection means, such as the microswitches 27, 28, 29, may be dispensed with, if the presence or absence of grid body 15b and the weight thereof are identified by detecting a suitable parameter varying when only the grid driving means such as motor is activated before the image sensing or by varying under the load applied to the motor during the image sensing operation. More specifically, the current flowing in the motor in the activated state is taken as a parameter, and such current in the equilibrium state is compared with predetermined current discrimination values to identify the presence or absence of the grid body 15b or the property thereof dependent on the weight thereof. The property of the grid body 15b dependent on the weight thereof may be the amount of lead metal in the grid 15b, namely the grid density.

Figure 5:
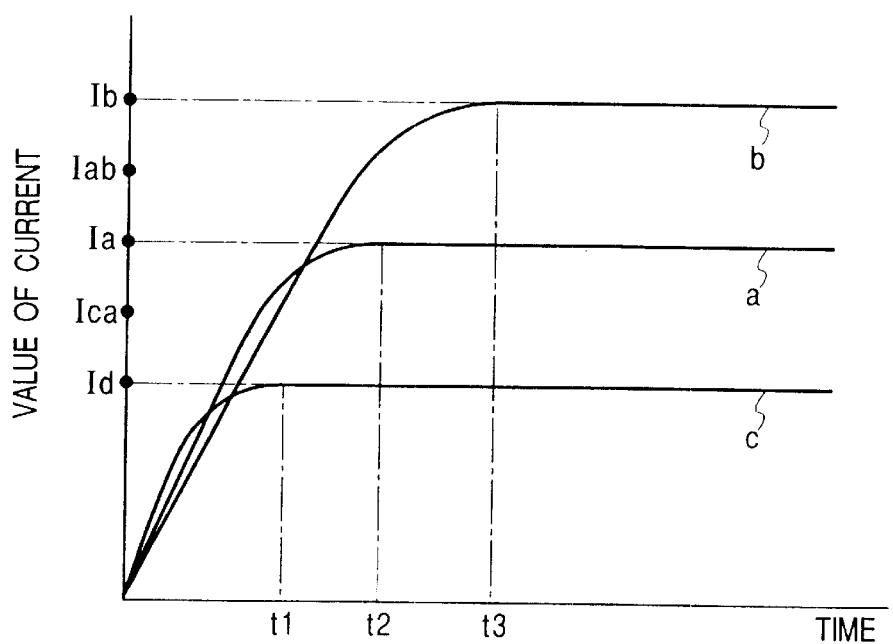
FIG. 5 is a chart showing the motor current as a function of time.

FIG. 5 is a chart showing the motor current as a function of time. In the absence of the grid body 15b in the X-ray image sensing unit 3, the motor is given only a limited torque so that the motor current from the start of rotation of the motor changes as indicated by a curve c, and the current reaches an equilibrium value Ic after an equilibrating time t1. Similarly, when the grid A or B is mounted, the current varies along a curve a or b to reach a value Ia or Ib after the equilibrating time t2 or t3. As the grid B is heavier with a higher grid density than the grid A, there is applied a larger load torque, so that Ib>Ia>Ic. Also the current increase rate at the start of rotation of the motor becomes larger in the order of b, a, c, and time required for equilibrating of current becomes longer in the order of t3>t2>t1.

By selecting the current discrimination values Ica, Iab so as to satisfy Ib>Iab>Ia>Ica>Ic, and if the current i after the current equilibrating time t3 is Ica>i, there can be identified the absence of the grid. Also if Iab>i>Ica or i>Iab, the mounting of the grid A or B can be identified, and in this manner it is rendered possible to identify the presence and absence of the grid and the kind thereof. In the present embodiment, the current in the equilibrium state is taken as the parameter varying according to the load applied to the grid drive means, but there may also be employed the current increase rate or the time until reaching the equilibrium state as such parameter, and the motor rotation which is reciprocally proportional to the load torque may be adopted with a similar effect.

Figure 6:
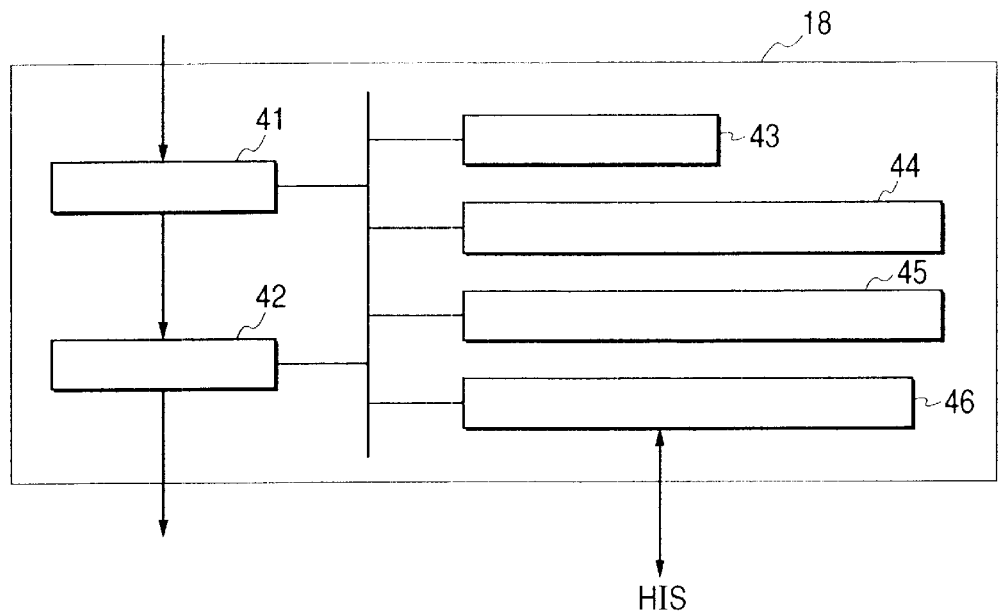
FIG. 6 is a block diagram of an image processing unit.

FIG. 6 is a block diagram of the image process unit 18, which can select a suitable image processing, utilizing the information on the presence and absence of the grid body 15b and the kind thereof, obtained as explained in the foregoing. The image process unit 18 is composed of a pre-process unit 41, a QA process unit 42, an image memory unit 43, an image process parameter memory unit 44, an adaptation grid table memory unit 45, and a network interface 46. The pre-process unit 41 and the QA process unit 42 execute in succession offset correction, logarithmic conversion, gain correction, grid erasing, frequency emphasis and gradation process.

At first there is executed offset correction for eliminating the fixed pattern specific to the radiation image detector 12 consisting of 2688×2688 channels. The fixed pattern means the values read from the channels of the radiation image detector 12, when it stands without X-ray irradiation for a period same as that for image data collection under X-ray irradiation after the resetting of the detector 12. More specifically, the image data of 14 bits obtained under X-ray irradiation are stored in a frame memory in the image process unit 18, then the fixed pattern of 14 bits (constituting the offset value) is obtained under the same condition as in the image data acquisition (same integrating time) but without X-ray irradiation and is stored in another frame memory, and the fixed pattern is subtracted from the image data. If a negative value is generated, it is rounded to 0, and the result of the subtraction is also regarded as 14-bit data.

After the offset correction, the logarithmic conversion converts the image data output from the radiation image detector 12 from a value corresponding to dose to a value corresponding to the absorption coefficient K of the substance in which the X-ray is attenuated by means of a look-up table. Also in the gain correction, assuming that the gain image has a reference value of 4095 while the fluctuation in the gain among the channels is with a range of ½ to 2, the logarithmic conversion table L(x) is set as:

$$L(x)=K \times 1n(x) \tag{1}$$

As explained in the foregoing, the output of the offset correction is 14-bit data with a value range of 0 to 16383 ($2^{14}$-1), so that a logarithmic table has to be constructed for proper output for these values.

As the gain correction is achieved by removing the gain image from the image data after offset correction, the output range of gain correction is from 1/8192 to 8. The coefficient K is to develop the range of 1/8192 to 8 into outputs of 16 bits, and can be determined as follows:

$$K=65535/\{1n(8)+1n(8192)\}=5909.19 \tag{2}$$

The gain correction intends the gain correction for the photoelectric conversion element of each pixel and also the 16-bit output after logarithmic conversion into corresponding 12-bit data.

Figure 7:
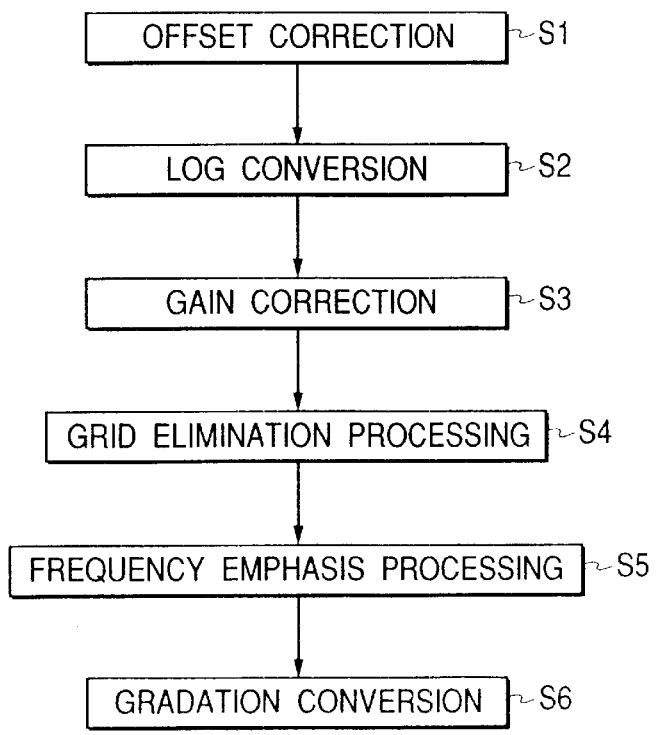
FIG. 7 is a flow chart showing pre-treatment and QA treatment.

FIG. 7 is a flow chart. For preparing a gain image, a step S1 acquires an offset correction image without the object 4 to 16 times, and the accumulated value for each pixel is taken as the image Wij (i=0 to 2687, j=0 to 2687).

Then a step S2 calculates the average A of the central area, utilizing the accumulated image Wij (i=0 to 2687, j=0 to 2687). The central area of the image consists of an area of 200×200 or 40,000 pixels at the center of the image.

A step S3 normalizes the accumulated image Wij with the average value A, thereby preparing a gain image having a reference value 4095 at the logarithmic conversion with the average A. More specifically, the gain image Sij, indicating the gain fluctuation in each pixel with respect to the reference value 4095, is given by:

$$Sij=Wij/A \times 4095 \ (i=0 \text{ to } 2687, j=0 \text{ to } 2687) \tag{3}$$

A step S4 applies the logarithmic conversion table L(Sij) shown in (1) to the gain image Sij, wherein K=5909.19 and L(Sij)=0 when Sij=0:

$$L(Sij)=int\{K \times 1n(Sij)+0.5\} \tag{4}$$

A step S5 obtains the difference of the logarithmic converted value L(Xij) of the X-ray irradiation data and the gain image as shown in (5), wherein the output Pij is 17-bit data with sign:

$$Pij=L(Sij)-L(Xij)=K \times 1n(Sij/Xij) \tag{5}$$

The 17-bit subtraction output data Pij with sign are converted into 12-bit data. As already explained in the logarithmic conversion, this conversion provides an output 0 when the X-ray irradiation data is 1/8192 of the normalized white image, and a 12-bit output 4095 when the X-ray irradiation data is 8 times.

The gain correction image is composed of an image without using a grid W1 regardless the presence and absence of the grid or the kind thereof. The gain image W1 is stored in the image memory unit 43, and, under the control of the pre-process unit 41 and according to the result of grid detection means, there is referred to an image process parameter table stored in the image process parameter memory unit 44 as shown in Tab. 1 and a matching gain image is downloaded from the image memory unit 43.

TABLE 1

| Grid | Gain image | Grid elimination | Frequency emphasis | Gradation |
|---|---|---|---|---|
| none | W1 | none | none | gamma 4.4 |
| A | W1 | with frequency Fa | with frequency F1 | gamma 4.0 |
| B | W1 | with frequency Fb | with frequency F2 | gamma 4.0 |
| C | W1 | with frequency Fc | with frequency F3 | gamma 4.0 |

Similarly the parameter for the grid elimination is controlled according to the presence and absence of the grid and the kind thereof. The grid elimination is executed only in the fixed grid system, but not used in the moving grid system. The image sensing with the fixed grid system has an advantage of faster image sensing but the stripe pattern of the grid is present in the image and may be disliked as a hindrance for diagnosis. Therefore, there is executed the grid elimination process for erasing the grid pattern present in the image by an image process.

For a given sampling frequency Fs of the radiation image detector 12, the frequency at which the stripe pattern is generated can be determined by calculation for each grid. If Fs>Fg where Fg is the grid frequency, the stripe pattern is generated at the frequency Fg and is removed by filtering. A band cut frequency Fa of the band-cut filter is selected from the image process parameter table stored in the image process parameter memory unit 44, according to the detection of the kind of the grid.

If Fs<Fg, the Moiree fringes are generated at Fs−(Fg−Fs)=2Fs−Fg. Also in this case, the band-cut filter is constituted by referring to the image process parameter table with the frequency 2Fs−Fg.

Also in the frequency process which is a QA process, the parameter is adjusted depending on the grid. This process is to restore the frequency region weakened as a by-effect of the grid elimination, and to enhance the frequency range effective for diagnosis without emphasizing the grid which is not completely eliminated. In the step S5, the parameters of these filters are determined from the image process parameter table, based on the grid information from the detection means.

Lastly, a step S6 executes a gradation process. In general, in image sensing without grid, the contrast of the entire image is slightly lowered because of the influence of the scattered light. In order to correct such phenomenon, it is desirable to elevate the contrast to perform conversion in the gradation process.

With respect to the table 1, there has been explained the process of varying the parameters according to the presence and absence of the grid and the kind thereof, but the process relating to the grid is not limited to the foregoing, and, also in the image compression in the post-process of the diagnostic image, the parameters may so be adjusted as not to emphasize the grid. Also the parameter adjusting method utilizing the grid information is not limited to those explained in the foregoing but may be suitably modified according to the desire of the doctors or radiologists.

As explained in the foregoing, the X-ray image sensing apparatus of the present embodiment can suppress the generation of shading by employing an image without using a grid for correction.

Many widely different embodiments of the present invention may be constructed without departing from the spirit and scope of the present invention. It should be understood that the present invention is not limited to the specific embodiments described in the specification, except as defined in the appended claims.

What is claimed is:

1. An image sensing method comprising:
    a detection step for detecting distribution of radiation transmitted by an object as an object image using sensor means; and
    a process step for processing and outputting the object image detected in said detection step,
    wherein, in said process step, gain correction for the object image is executed employing a gain correction image obtained on the basis of an image detected by the sensor means without the object and without using a grid for reducing scattered radiation from the object, regardless of the presence or absence of such grid.

2. An image sensing method according to claim 1 wherein the gain correction image used in said process step is obtained by taking a ratio of each pixel of the image detected without the object and without using the grid to a reference value which is an average of a part of the image detected without the object and without using the grid.

3. An image sensing method comprising:
    an image detection step for detecting distribution of radiation transmitted by an object as an object image using sensor means;
    a grid detection step for detecting at least one of kind, presence and absence of a grid for reducing scattered radiation from the object; and
    a process step for processing and outputting the object image detected in said image detection step,
    wherein, in said process step, gain correction for the object image is executed employing a gain correction image obtained on the basis of an image detected by the sensor means without the object and without using the grid, regardless of a detection result in said grid detection step.

4. An image sensing method according to claim 3, wherein the gain correction image used in said process step is obtained by taking a ratio of each pixel of the image detected without the object and without using the grid to a reference value which is an average of a part of the image detected without the object and without using the grid.

5. An image sensing method comprising:
    a detection step for detecting distribution of radiation transmitted by an object as an object image using sensor means;
    a process step for processing and outputting the object image detected using a grid for reducing scattered radiation from the object in said detection step,
    wherein, in said process step, gain correction for the object image is executed employing a gain correction image obtained on the basis of an image detected by the sensor means without the object and without using the grid.

6. An image sensing method according to claim 5, wherein the gain correction image used in said process step is obtained by taking a ratio of each pixel of the image detected without the object and without using the grid to a reference value which is an average of a part of the image detected without the object and without using the grid.

7. An image processing apparatus comprising:
    a process unit for processing and outputting an object image which designates distribution of radiation transmitted by an object; and
    an image memory unit for storing a gain correction image for gain correction for the object image,
    wherein the gain correction image stored in said image memory unit is obtained on the basis of an image obtained without the object and without using a grid for reducing scattered radiation from the object, and is employed by said process unit in the gain correction for the object image, regardless of the presence or absence or such grid.

8. An image processing apparatus according to claim 7, wherein said process unit obtains the gain correction image by taking a ratio of each pixel of the image obtained without the object and without using the grid to a reference value which is an average of a part of the image obtained without the object and without using the grid.

9. An image processing apparatus comprising:
    a process unit for processing and outputting an object image which designates distribution of radiation transmitted by an object; and
    a grid information receiving unit for receiving information of a grid for reducing scattered radiation from the object which is at least one of kind, presence and absence of the grid,
    wherein said process unit executes gain correction for the object image employing a gain correction image obtained on the basis of an image obtained without using the object and without using the grid, regardless of information received by said grid information receiving unit.

10. An image processing apparatus according to claim 9, wherein said process unit obtains the gain correction image by taking a ratio of each pixel of the image obtained without the object and without using the grid to a reference value which is an average of a part of the image obtained without the object and without using the grid.

11. An image processing apparatus comprising:

a process unit for processing and outputting an object image which designates distribution of radiation transmitted by an object and is obtained using a grid for reducing scattered radiation from the object; and an image memory unit for storing a gain correction image for gain correction for the object image, wherein the gain correction image stored in said image memory unit is obtained on the basis of an image obtained without the object and without using the grid, and is employed by said process unit in gain correction for the object image.

12. An image processing apparatus according to claim 11, wherein said process unit obtains the gain correction image by taking a ratio of each pixel of the image obtained without the object and without using the grid to a reference value which is an average of a part of the image obtained without the object and without using the grid.

13. An image sensing system comprising;

a radiation generation unit for emitting radiation;

a sensing unit for detecting distribution of radiation emitted from said radiation generation unit and transmitted by an object as an object image; and a process unit for processing and outputting the object image detected by said sensing unit, wherein said process unit executes gain correction for the object image employing a gain correction image obtained on the basis of an image detected by the sensing unit without the object and without using a grid for reducing scattered radiation from the object, regardless of the presence or absence of such grid.

14. An image sensing system according to claim 13, wherein said process unit obtains the gain correction image by taking a ratio of each pixel of the image detected by said sensing unit without the object and without using the grid to a reference value which is an average of a part of the image directed by said sensing unit without the object and without using the grid.

15. An image sensing system comprising:

a radiation generation unit emitting radiation;

a sensing unit for detecting distribution of radiation emitted by said radiation generation unit and transmitted by an object as an object image;

a detection unit for detecting at least one of kind, presence and absence of a grid for reducing scattered radiation from the object; and a process unit for processing and outputting the object image detected by said sensing unit, wherein said process unit executes gain correction for the object image employing a gain correction image obtained on the basis of an image detected by said sensing unit without the object and without using the grid, regardless of a detection result of said detection unit.

16. An image sensing system according to claim 15, wherein said process unit obtains the gain correction image by taking a ratio of each pixel of the image detected by said sensing unit without the object and without using the grid to a reference value which is an average of a part of the image detected by said sensing unit without the object and without using the grid.

17. An image sensing system comprising:

a radiation generation unit for emitting radiation;

a sensing unit for detecting distribution of radiation emitted by said radiation generation unit and transmitted by an object as an object image;

a process unit for processing and outputting the object image detected using a grid for reducing scattered radiation from the object by said sensing unit, wherein said process unit executes gain correction for the object image employing a gain correction image obtained on the basis of an image detected by the sensing unit without the object and without using the grid.

18. An image sensing system according to claim 17, wherein said process unit obtains the gain correction image by taking a ratio of each pixel of the image detected by said sensing unit without the object and without using the grid to a reference value which is an average of a part of the image detected by said sensing unit without the object and without using the grid.

19. An image processing method comprising:

a process step for processing and outputting an object image which designates distribution of radiation transmitted by an object; and a download step for downloading a gain correction image stored in an image memory unit for gain correction for the object image, wherein the gain correction image stored in said image memory unit is obtained on the basis of an image obtained without the object and without using a grid for reducing scattered radiation from the object, and is employed in gain correction for the object image in said process step regardless of the presence or absence of such grid.

20. An image processing method according to claim 19, wherein the gain correction image used in said process step is obtained by taking a ratio of each pixel of the image obtained without the object and without using the grid to a reference value which is an average of a part of the image obtained without the object and without using the grid.

21. An image processing method comprising:

a process step for processing and outputting an object image which designates distribution of radiation transmitted by an object; and a receiving step for receiving information of a grid for reducing scattered radiation from the object which is at least one of kind, presence and absence of the grid, wherein, in said process step, gain correction for the object image is executed employing a gain correction image obtained on the basis of an image obtained without the object and without using the grid, regardless of information received in said receiving step.

22. An image processing method according to claim 21, wherein the gain correction image used in said process step is obtained by taking a ratio of each pixel of the image obtained without the object and without using the grid to a reference value which is an average of a part of the image obtained without the object and without using the grid.

23. An image processing method comprising:

a process step for processing and outputting an object image which designates distribution of radiation transmitted by an object and is obtained using a grid for reducing scattered radiation from the object; and a download step for downloading a gain correction image stored in an image memory unit for gain correction for the object image, wherein the gain correction image stored in said image memory unit is obtained on the basis of an image obtained without the object and without using the grid, and is employed in gain correction for the object image in said process step.

24. An image processing method according to claim 23, wherein the gain correction image used in said process step is obtained by taking a ratio of each pixel of the image obtained without the object and without using the grid to a reference value which is an average of a part of the image obtained without the object and without using the grid.

* * * * *

UNITED STATES PATENT AND TRADEMARK OFFICE
CERTIFICATE OF CORRECTION

PATENT NO.    : 6,507,038 B2                               Page 1 of 1
DATED         : January 14, 2003
INVENTOR(S)   : Osamu Tsujii It is certified that error appears in the above-identified patent and that said Letters Patent is hereby corrected as shown below:

Column 1,
Line 27, "florescent" should read -- fluorescent --.

Column 3,
Line 23, "following" should read -- follow --.

Column 7,
Line 58, "claim 1" should read -- claim 1, --.

Column 8,
Line 49, "or" should read -- of --.

Column 9,
Line 28, "comprising;" should read -- comprising: --; and
Line 50, "unit" should read -- unit for --.

Signed and Sealed this

Thirtieth Day of September, 2003

JAMES E. ROGAN
*Director of the United States Patent and Trademark Office*